United States Patent
Müller

[19]
[11] Patent Number: 5,871,459
[45] Date of Patent: Feb. 16, 1999

[54] APPARATUS FOR TREATING BLOOD

[76] Inventor: Hans Müller, Reichenhaller Str. 49, 81547 München, Germany

[21] Appl. No.: 835,345

[22] Filed: Apr. 7, 1997

Related U.S. Application Data

[63] Continuation of Ser. No. 604,585, Feb. 21, 1996, abandoned.

[30] Foreign Application Priority Data

Feb. 22, 1995 [DE] Germany .................. 195 06 163.2

[51] Int. Cl.⁶ ............................................ A61M 37/00
[52] U.S. Cl. .............................. 604/4; 422/45; 422/24
[58] Field of Search ..................... 422/45, 24; 604/4–6

[56] References Cited

U.S. PATENT DOCUMENTS

| | | | |
|---|---|---|---|
| 2,827,901 | 3/1958 | Jones | 422/45 |
| 4,661,092 | 4/1987 | Popovich et al. | 422/45 |
| 4,968,483 | 11/1990 | Muller et al. | 422/45 |

FOREIGN PATENT DOCUMENTS

| | | |
|---|---|---|
| 2 082 819 | 11/1971 | France . |
| 26 24 305 | 2/1978 | Germany . |
| 3521802 | 1/1987 | Germany . |
| 43 40 730 | 6/1995 | Germany . |
| 432 40 730 | 6/1995 | Germany . |
| 4340730 | 6/1995 | Germany . |
| 4410411 | 10/1995 | Germany . |

*Primary Examiner*—John G. Weiss
*Assistant Examiner*—Ki Yong O
*Attorney, Agent, or Firm*—Klaus J. Bach

[57] ABSTRACT

In an apparatus for the extra-corporal treatment of blood wherein blood is supplied from a body to a vacuum bottle via a conduit and an insertion spike, the insertion spike is in communication, by way of a gas hose, with a pressure compensation bag from which a predetermined amount of gas can be supplied to the insertion spike for foaming the blood in the vacuum bottle, whereby no excess pressure can be generated in the vacuum bottle. The blood conduit further includes a quartz glass portion to permit UV irradiation of the blood while passing therethrough.

8 Claims, 3 Drawing Sheets

APPARATUS FOR TREATING BLOOD

This application is a continuation, of application Ser. No. 08/604,585, filed Feb. 21, 1996 now abandoned.

BACKGROUND OF THE INVENTION

The invention relates to an apparatus for treating blood taken from a human body or an animal.

Apparatus for the treatment of human or animal blood with oxygen, activated oxygen or with so-called Singuletoxygen are generally known. The use of oxygen-containing treatment agents will be designated below by the expression "gas treatment". With this treatment, the blood taken is subjected to gas in a vacuum bottle or a plastic bag and is then returned to the human or animal blood vessels. Such apparatus are described in DE OS 12 38 884 and 43 40 730; they are used for the oxygen enrichment of the blood.

DE OS 35 21 802 discloses an apparatus for the gas treatment of blood by the hematogen oxidation therapy (HOT), wherein, during removal from a body, the blood is pumped into a collection container into which, subsequently, an apparatus for the HOT therapy is inserted. According to this publication, the blood is foamed in the collection container by the addition of oxygen, and is then forced, by the excess pressure generated with the addition of oxygen, through a quartz glass bulb into a second collection container. During the transfer, the foamed blood is subjected to UV radiation. From the second collection container, the blood is returned to the blood vessels.

DE OS 44 10 411 discloses an apparatus for the extra-corporal treatment of blood which, instead of a vacuum bottle, uses a flexible blood bag which facilitates HOT treatment and provides a completely mounted re-transfusion set which, altogether, is contained in a relatively small package in a sterile manner. However, since no vacuum is employed for the removal of blood, the blood removal procedure is relatively time consuming.

For this reason, methods which use vacuum bottles are still in wide use since they permit rapid removal of the blood.

A problem encountered with the gas treatment of blood is caused by the fact that the gas is supplied from a high pressure storage bottle by way of a pressure reducing valve. the pressure reducing valves generally used can usually be adjusted only to a relatively high discharge pressure so that it is difficult to avoid the formation of excess pressure in the vacuum bottle or in the blood bag during the gas treatment.

It is therefore the object of the present invention to provide a procedure by which the desired amount of gas can be supplied to the blood in a simple manner without the generation of excess pressure in the vacuum bottle or in the blood bag.

SUMMARY OF THE INVENTION

In an apparatus for the extra-corporal treatment of blood wherein blood is supplied from a body to a vacuum bottle via a conduit and an insertion spike, the insertion spike is in communication, by way of a gas hose, with a pressure compensation bag from which a predetermined amount of gas can be supplied to the insertion spike for foaming the blood in the vacuum bottle utilizing the vacuum remaining in the vacuum bottle after the blood is supplied thereto, whereby no excess pressure can be generated in the vacuum bottle. The blood conduit further includes a quartz glass portion to permit UV irradiation of the blood while passing therethrough.

By providing, in the gas supply line, a pressure compensation bag, the bag can be filled with a predetermined amount of gas which is sufficient for the gas treatment of the blood without generating an excessive pressure in the vacuum bottle or in the blood bag. When larger amounts of gas are necessary, the pressure compensation bag can be filled more than one time.

With the arrangement according to the invention, the development of excess pressure in the vacuum bottle or in the blood bag which is undesirable for the retransfusion of the blood can be prevented in a simple manner.

According to one embodiment of the invention, the elastic pressure compensation bag is pleated.

With a particular design of the insertion spike, the gas supplied for the gas treatment can be introduced into the blood by way of a diffusion body.

The advantages and particular features of the invention will be apparent from the following description of an embodiment on the basis of the enclosed drawings.

DESCRIPTION OF A PREFERRED EMBODIMENT

Figure 1:
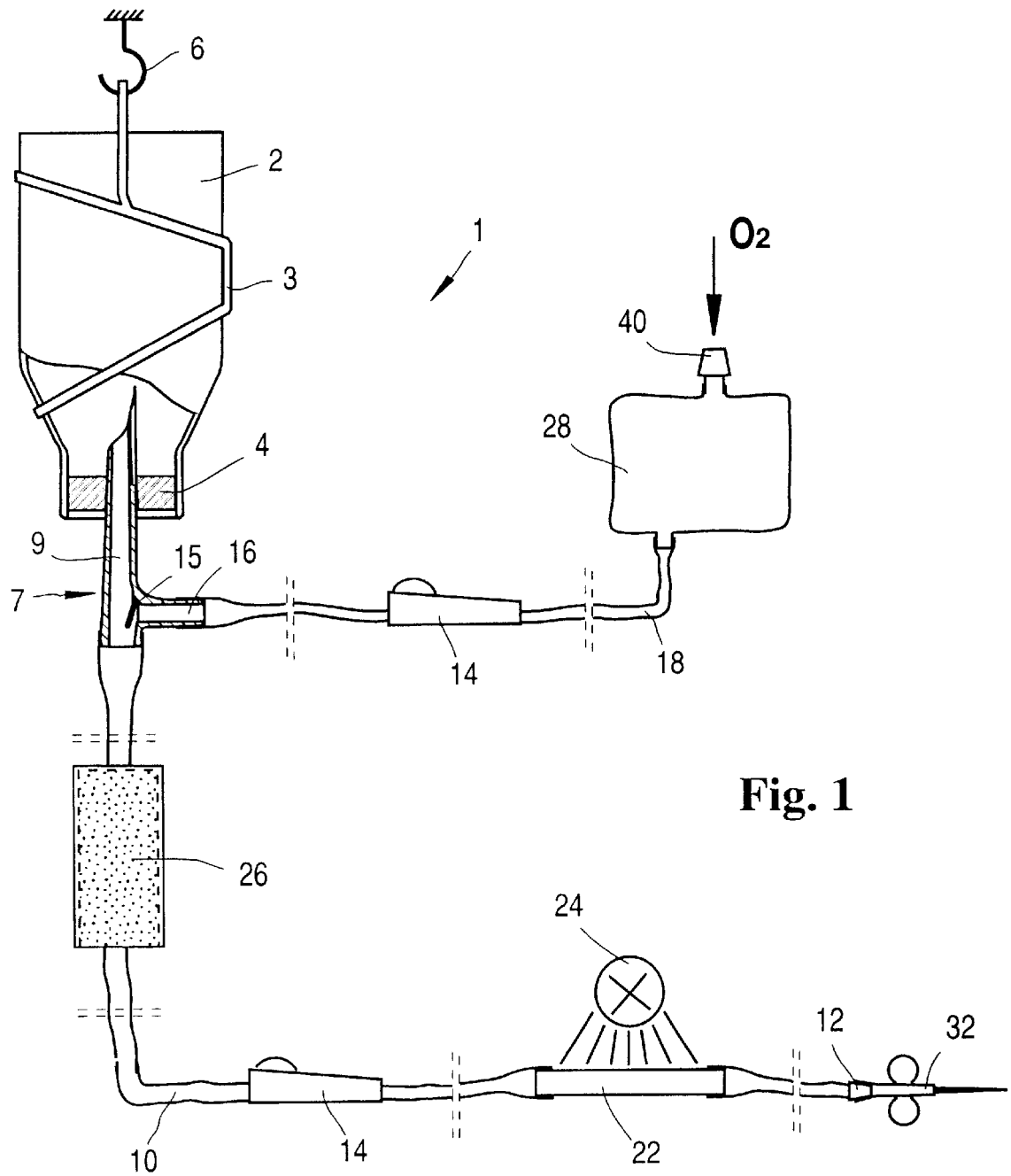
FIG. 1 shows a retransfusion set according to the invention.

FIG. 1 shows a retransfusion set for the gas treatment of blood which, with the exception of the vacuum bottle 2 can be provided as a preassembled instrument packaged in a sterile, sealed set. The set comprises a vacuum bottle 2, which may be supported from a hook 6 by way of a suspension structure 3. The bottle is closed by a rubber plug 4 which is pierced by an insertion spike 7 having a passage 9 which provides for communication with a blood filter 26 and also with a gas connection 16 by way of a gas valve 15.

From the gas filter 26, a blood hose 10 leads to a quartz tube 22 and then, via a coupling piece 12 to a winged cannula 32. Between the glass tube 22 and the blood filter 26, a roller clamp 14 is mounted on the blood hose 10 by which the blood hose can be pinched off. Adjacent the quartz tube 22, there is a UV light source 24.

Connected to gas connection 16 is a gas hose 18 which is also provided with a roller clamp 14 for pinching off the gas hose. The gas hose 18 is connected to the pressure compensation bag 28 which includes a coupling 40 for the connection of a gas source. The gas source is usually a high pressure gas storage bottle from which the gas can be supplied to the pressure compensation bag via a pressure reducing valve. However, the pressure provided by such gas pressure reduction valve is usually too high so that direct admission of the gas to the vacuum bottle leads to excessive pressures in the vacuum bottle. An additional pressure reducing valve is necessary to reduce this pressure before the retransfusion of the blood supply into the body.

With the use of a pressure compensation bag 28, the formation of such an undesirably high pressure in the vacuum bottle can be avoided.

Figure 2:
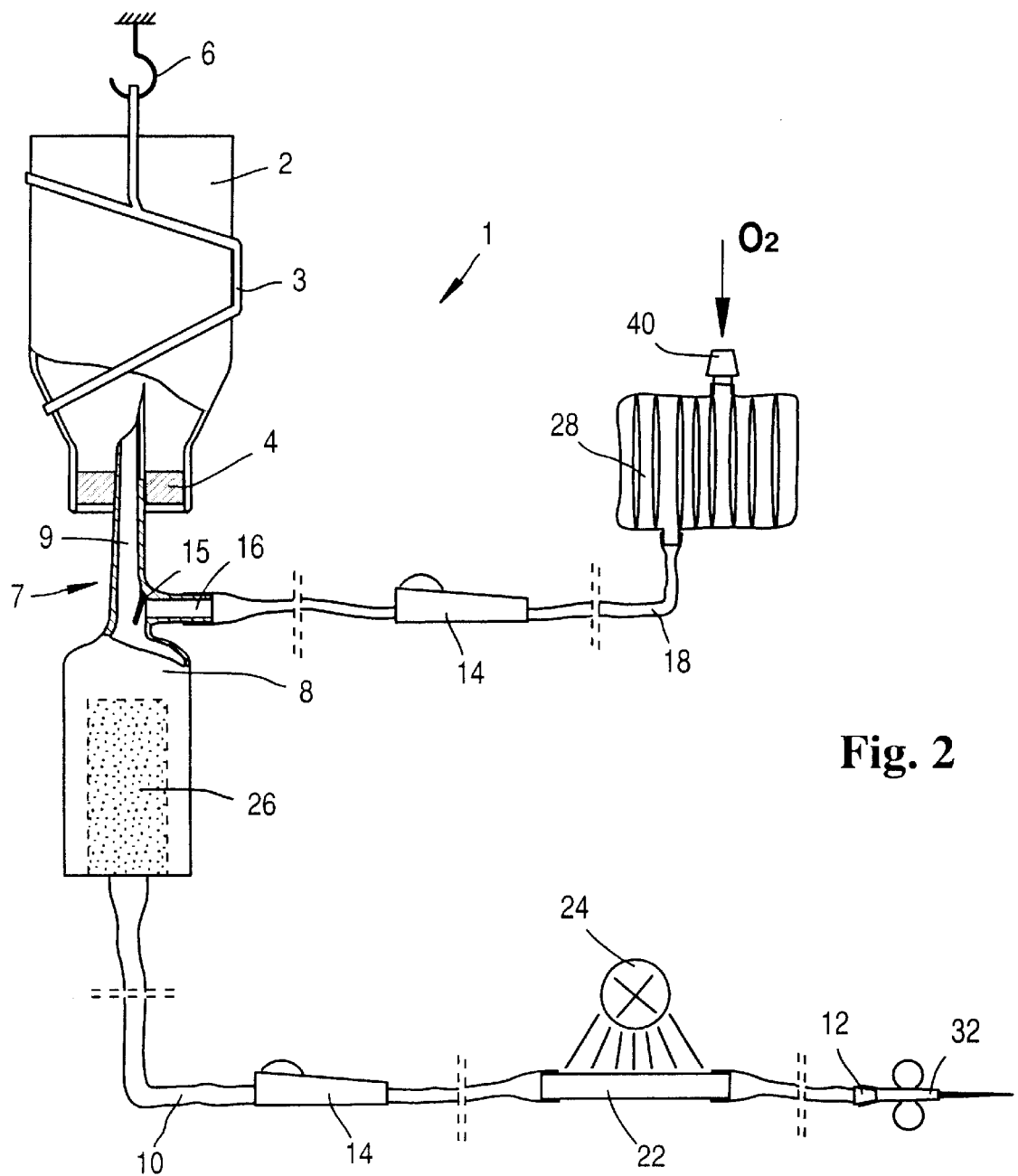
FIG. 2 shows another embodiment of the retransfusion set.

FIG. 2 shows an embodiment of the invention wherein the blood filter 26 and an inspection glass 8 are combined to a single unit.

Blood can be treated with the retransfusion set according to the invention in the following manner:

At the beginning of the treatment, the integral retransfusion set which includes several components is removed from a sterile package and the insertion spike 7 is inserted through the rubber plug 4 of the vacuum bottle 2. Also, the coupling 40 of the pressure compensation bag 28 is connected to a gas source under pressure which may be for example, an oxygen bottle with a pressure reducing valve. Such pressure reducing valves can reduce the pressure of the gas leaving the bottle only to values which are still too high for safe handling of the retransfusion set.

To remove the blood, a blood vessel is punctured by the winged cannula 32 and the blood is sucked through the blood hose 10, the opened roller clamp 14 and the blood filter 26 into the vacuum bottle 2.

For the treatment of the blood with the gas, the roller clamp 14' on the blood hose 10 is closed and the roller clamp 14 on the gas hose 18 is opened. This permits the gas which is maintained in the the pressure compensation bag at a small excess pressure with respect to normal atmospheric pressure, to flow into the vacuum bottle by way of the gas connection 16, the gas valve 15 and the passage 9 of the insertion spike 7, whereby the blood in the vacuum bottle is foamed and, at the same time, the vacuum in the vacuum bottle is reduced. If the amount of gas present in the pressure compensation bag 28 corresponds to the amount needed for the reduction of the vacuum in the vacuum bottle, the gas treatment of the blood results in a pressure reduction to normal pressure so that the blood in the vacuum bottle is now available for retransfusion, essentially under normal pressure. For returning the blood to the blood vessels, the roller clamp 14' on the blood hose 10 is opened. The roller clamp 14 on the gas hose 18 remains open at the same time so that the pressure can be equalized during retransfusion of the blood. For this purpose, a residual amount of gas in the pressure equalizing bag 28 is utilized or gas is permitted to enter through the open coupling 40. During retransfusion, the blood foamed with oxygen which flows back through the quartz tube 22 via the winged cannula 32 to the vessels is irradiated by a UV light source 24. Instead of an UV light source, also a wide band light source may be used.

If the vacuum bottle 2 is suspended from a hook 6 during retransfusion of the blood, the return flow of the blood to the blood vessels against the blood pressure in the vessels can be adjusted by adjustment of the height at which the bottle 2 is supported. The arrangement offers the possibility to irradiate the blood during removal from the blood vessels as well as during its return. In this way, the time required for the hematogen oxidation therapy can be reduced.

Figure 3:
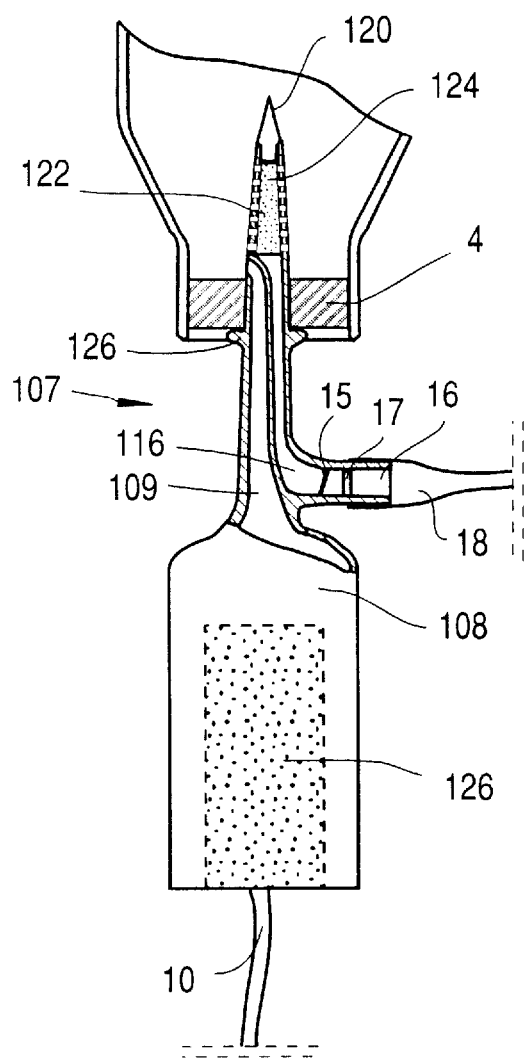
FIG. 3 shows an inspection glass with an insertion spike and with a diffusion body.

A particularly advantageous embodiment including a sight glass 108 is shown in FIG. 3. It differs from other glasses in that the gas connection 16 in the insertion spike 107 leads to the tip of the spike through a separate passage 116. The insertion spike 107 is provided with a steel tip 120 which is cast into the spike and, behind the steel tip 120, the insertion spike includes a diffusion body 122. The wall area of the insertion spike adjacent the diffusion body 122 is perforated like a sieve with small holes 124 so that the gas supplied through the gas hose 18 enters the vacuum bottle 2 in an atomized form. The finely distributed gas bubbles greatly increase the efficiency of the gas treatment.

To insure that during insertion of the spike through the rubber plug 4, the outlet and inlet openings for the blood are safely located within the vacuum bottle 2 the spike is provided with a shoulder 126 intended to abut the surface of the rubber plug 4 when the spike is inserted.

Finally, the gas tube 16 includes a bacteria filter 17 arranged adjacent the gas valve 15.

Figure 4:
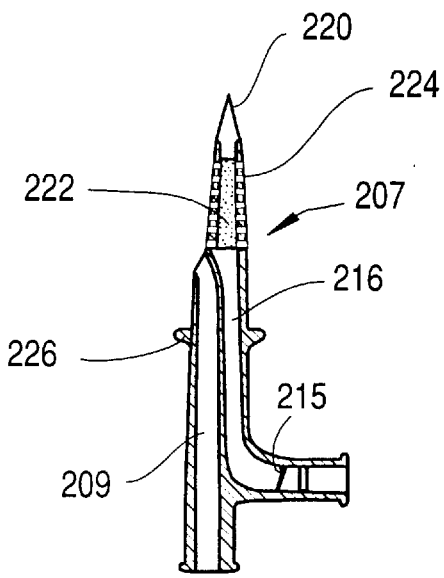
FIG. 4 shows an insertion spike.

FIG. 4 shows an insertion spike 207 which is similar to that shown in FIG. 3 but is not formed integrally with the sight glass. Such an insertion spike is particularly suitable for use with an arrangement as shown in FIG. 1.

If the diffusion body is arranged within the spike of the sight glass 8 or 108, respectively, the retransfusion set becomes very practical and, at the same time, the set becomes less expensive than prior art arrangements.

A major advantage of the arrangement according to the invention is seen in the fact that the control afforded in the admission of the gas medium for the foaming of the blood insures that the formation of an excessive gas pressure in the vacuum bottle is avoided. The pressure compensation bag facilitates a dosed admission of gas in a predetermined amount, since a sufficient gas reservoir can be provided in the pressure compensation bag so that, during foaming of the blood, no excess pressure is generated in the vacuum bottle. As a result, a residual vacuum in the vacuum bottle after blood is taken is easily deployed and the gas needed for the foaming of the blood is introduced in an atomized form and in the desired amount without the generation of an excessive pressure in the vacuum bottle.

What is claimed is:

1. Apparatus for the extra-corporal treatment of blood taken from a human body or an animal with oxygen, said apparatus comprising: a vacuum bottle having a closure plug and being under a predetermined vacuum, an insertion spike for piercing said closure plug of said vacuum bottle, a blood-conducting conduit having one end connected to said spike and having a coupling piece at the other end thereof for mounting thereon a cannula for insertion into a blood vessel, said conduit including a blood filter, a flow control device and a quartz glass tube through which the blood is conducted on its way from said cannula to said vacuum bottle and from said vacuum bottle back to said cannula, and an elastic pressure compensation bag containing the oxygen for the treatment of the blood in said vacuum bottle, said bag being in communication with said insertion spike by way of a gas hose extending between said pressure compensation bag and said insertion spike and including a gas flow control means for controlling the flow of gas from said pressure compensation bag to said vacuum bottle.

2. An apparatus according to claim 1, wherein said pressure compensation bag consists of a pleated plastic material.

3. An apparatus according to claim 1, wherein said blood filter is disposed within a sight glass connected to said insertion spike.

4. An apparatus according to claim 1, wherein all components of said apparatus are interconnected and are provided as an integral unit ready for use.

5. An apparatus according to claim 1, wherein said insertion spike includes a steel tip cast into the front end of said spike and has a first passage with a connecting piece connected to said gas hose and leading to said front end, and a diffusion body received in said passage adjacent said steel tip, said spike having perforated walls adjacent said diffusion body.

6. An apparatus according to claim 5, wherein said insertion spike includes a second passage in communication with said blood conduit and leading to an opening in a side of said insertion spike adjacent said diffusion body.

7. An apparatus according to claim 6, wherein said insertion spike is provided with a shoulder disposed at a predetermined distance from said opening such that, when said insertion spike has pierced said closure plug and said shoulder abuts said closure plug, said opening is disposed within said vacuum bottle.

8. An apparatus according to claim 1, wherein said insertion spike includes a connecting piece for connection to said gas hose with a check valve for preventing blood from entering said connecting piece.

* * * * *